United States Patent [19]

Lamb et al.

[11] Patent Number: 5,055,563
[45] Date of Patent: Oct. 8, 1991

[54] CONTINUOUS PREPARATION OF AROMATIC DIAZONIUM FLUORIDE SALTS FROM CORRESPONDING AROMATIC AMINES

[75] Inventors: Bruce J. Lamb, St. Charles; Nickolas J. Stepaniuk, Chesterfield, both of Mo.

[73] Assignee: Mallinckrodt Specialty Chemicals Company, St. Louis, Mo.

[21] Appl. No.: 538,056

[22] Filed: Jun. 13, 1990

[51] Int. Cl.$^5$ .......................... C07C 245/20
[52] U.S. Cl. ........................................ 534/565
[58] Field of Search ............................. 534/565

[56] References Cited

U.S. PATENT DOCUMENTS

| | | | |
|---|---|---|---|
| 2,563,796 | 8/1951 | Shenk et al. | 534/565 X |
| 2,606,183 | 8/1952 | Head et al. | 534/565 |
| 2,705,730 | 11/1955 | Head | 534/565 X |
| 2,854,479 | 9/1958 | Britton et al. | 534/565 X |
| 3,117,954 | 1/1964 | Hupfer | 534/565 |
| 3,160,623 | 12/1964 | Anello et al. | 534/565 |
| 3,423,391 | 1/1969 | Kindler et al. | 534/565 |
| 4,233,213 | 11/1980 | Breig et al. | 534/565 |
| 4,234,478 | 11/1980 | Atherton et al. | 534/565 X |
| 4,246,171 | 1/1981 | Hamilton et al. | 534/565 |
| 4,268,437 | 5/1981 | Behringer et al. | 534/565 |
| 4,820,807 | 4/1989 | Arnold et al. | 534/565 |
| 4,886,920 | 12/1989 | Cantrell | 534/565 X |
| 4,918,168 | 4/1989 | Stepaniuk et al. | 534/565 |

FOREIGN PATENT DOCUMENTS

| | | | |
|---|---|---|---|
| 2825655 | 12/1979 | Fed. Rep. of Germany | 534/565 |
| 844062 | 8/1960 | United Kingdom | 534/565 |

OTHER PUBLICATIONS

Pierce, Chem. & Engr. News, vol. 39, No. 17, pp. 65 to 66 (04-24-1961).

*Primary Examiner*—Mary C. Lee
*Attorney, Agent, or Firm*—Rothwell, Figg, Ernst & Kurz

[57] ABSTRACT

Disclosed is a process for continuous preparation of aromatic diazonium fluoride salts wherein diazotizable aromatic primary amines are continuously diazotized in a series of continuous-stirred tank reactors, wherein a portion of a premixed diazotization solution is cooled prior to being continuously fed into each of the reactors.

18 Claims, 3 Drawing Sheets

CONTINUOUS PREPARATION OF AROMATIC DIAZONIUM FLUORIDE SALTS FROM CORRESPONDING AROMATIC AMINES

BACKGROUND OF THE INVENTION

This invention relates to a process for the continuous preparation of aromatic diazonium fluoride salts.

Diazotization of aromatic primary amines to prepare aromatic diazonium fluorides is of considerable importance in that such diazonium compounds are commercially valuable intermediates which can be converted to dyes (e.g. amino azobenzene) and aromatic fluorides which are useful as intermediates in preparing various pesticides, pharmaceuticals and other products.

Various processes have been used in the past to prepare aromatic-fluoro compounds. None of these prior art processes has proven entirely satisfactory. For example, Japanese patent publication No. 81330-74 describes a process for the preparation of aromatic fluoro compounds on a laboratory, as opposed to an industrial, scale. Diazotization of a substituted or unsubstituted amino compound and the thermal decomposition of the diazonium salt produced by diazotization are carried out in one step at the thermal decomposition temperature of the diazonium salt. A solution of a compound that gives nitrous acid first is dissolved in hydrofluoric acid and then allowed to act on an aromatic amino compound. No methods are suggested for removing the heat produced from this reaction. The examples set forth in the patent illustrate batchwise procedures.

German Pat. No. 600,706 relates to a batch-wise process for the production of fluoro aromatic compounds. The diazotization and decomposition are carried out in the presence of excess anhydrous, or practically anhydrous, hydrogen fluoride. An aromatic amine is dissolved in hydrogen fluoride, and a diazotization agent such as dry sodium nitrite slowly is added over the course of one hour. During this process the temperature is held to about 5° C. This process also is discussed by Ferm et al. in J.A.C.S. 72:4809–4810 (1950). Experimenting on a small-scale, Ferm et al. confirmed the utility of the above-process for a number of fluoroaromatics in batch-wise procedures. None of these processes is amenable to the continuous industrial production of fluoro-aromatics in high yields.

Various processes for the continuous production of fluoro-aromatics also are known. For example, Hupfer, U.S. Pat. No. 3,117,954, describes a crossflow cascaded reactor for the continuous aqueous solution of sodium nitrite. Agitation is limited to effect sedimentation.

Hamilton, et al, U.S. Pat. No. 4,246,171, discloses a continuous diazotization process in which the rate of addition of the inorganic nitrite is controlled by a polarovoltric method. An aqueous solution of an amine in an acid and a solution of an inorganic nitrite are added continuously and regularly to a reactor. The addition of the solution of inorganic nitrite is automatically regulated to ensure that a preselected concentration of unreacted nitrous acid is maintained in the reactor throughout the entire reaction period. Hamilton et al. recognize that amines which give a fast diazotization reaction rapidly produce a very large amount of heat. Hamilton et al. also recognize that unwanted by-products will form if the temperature rises too high. The use of flaked or crushed ice is suggested to control this rise in temperature.

Aqueous systems typically result in lower yields, about 50% after decomposition. Moreover, the use of aqueous systems in conjunction with HF systems results in additional problems, such as increased corrosion of the reaction vessels.

Prior art diazotization processes have not proven completely satisfactory. They typically are not amenable to a continuous process or are complex, inefficient, expensive and/or prone to result in an unacceptably high level of unwanted by-products. Most of these deficiencies are caused by the problem of the tremendously exothermic nitrite/HF and diazotization reactions.

Accordingly, there is a substantial need in the art for a continuous diazotization process which would overcome the disadvantages of heretofore known processes.

SUMMARY OF THE INVENTION

The present invention substantially fulfills the above-described need and overcomes the above-noted deficiencies in the processes of the prior art in a simple, efficient and inexpensive manner by providing a continuous process wherein an aromatic amine is continuously diazotized to a diazonium fluoride in the presence of hydrogen fluoride in a multi-reactor system with close control of temperature throughout the reaction mixture. As a means of removing the heat of reaction, a diazotizing species is pre-made as a solution in hydrogen fluoride (HF). This permits a significant amount of the heat of reaction to be removed from the system prior to the desired diazotization reaction. The damaging effect of high local heat produced by the diazotization agent/HF reaction is thereby reduced, thus reducing yield losses due to decomposition. Use of a solution of diazotizing agent also reduces the formation of corrosive by-products and their corrosive effects.

In one embodiment of the invention, a solution of a diazotizing agent and hydrogen fluoride is premade and the heat from this reaction removed. This diazotization solution is continuously introduced through a parallel series of inputs into each of a series of reactors where it is mixed with a premixed aromatic amine-hydrogen fluoride solution which is continuously being serially fed into the first reactor and overflowing from there into the second and so on, through each reactor of the reactor series. In each reactor the two entering solutions are mixed. Simultaneously with the introduction of the solutions, heat is removed from each reactor, such that the temperature is less than the autothermal decomposition temperature of said mixture.

DETAILED DESCRIPTION OF THE PREFERRED EMBODIMENT

Figure 1:
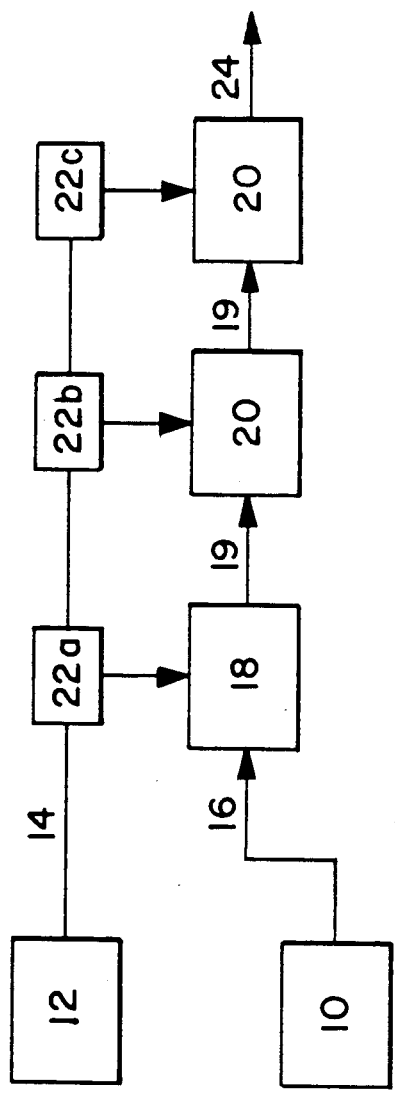
FIG. 1 is a schematic flow diagram of the process wherein 3 continuously stirred tank reactors are sequentially connected.

In accordance with one embodiment of the invention, as illustrated in FIG. 1, an amine-hydrogen fluoride solution (HF) and a diazotization solution are prepared in vessels 10 and 12, respectively. Each vessel has means to effect temperature control of the solution contained therein. The temperature control means can be through the use of jacketed reactors and, if necessary, additional cooling such as coils and external heat exchangers, depending on the scale, materials of construction and product character. The control of the temperature can be automated to keep the reactor contents within 1°-2° C. of a target temperature by regulating the flow of coolant. The diazotization solution is passed via outlet conduit 14 to a flow ratio device 22a where a portion of the total flow is diverted and fed into a continuous stirred tank reactor (CSTR) 18. Meanwhile, the amine-HF solution is passed from solution vessel 12 to outlet conduit 16 and fed into CSTR 18. Here, it is mixed with a portion of the diazotization solution. CSTR 18 is permitted to overflow through overflow conduit 19 into CSTR 20 where it is mixed with diazotization solution from flow ratio device 22b. This overflow process is repeated until all of the diazotization solution has been reacted. Each reactor in the series preferably is maintained at a controlled temperature by a cooling means (not shown). From the last CSTR in the series, the product diazonium solution can be transferred, 24, to a decomposition vessel (not shown) where it can be decomposed to produce the desired aromatic fluoride with substantial freedom from tar and other by-products.

The number of stages will be dictated by the desired scale of operation, the reaction kinetics of the diazotization, and reactor heat transfer duty and design. It will also be dictated by the stability of the diazonium to reaction conditions at the diazotizer injection point. It is preferable to use a greater number of smaller, better mixed vessels which provide greater local temperature control at the mixing zone. It is conceivable that one CSTR stage could suffice for some diazonium makeups, given a very stable molecule and no side reaction risks. In general, the performance advantages of multistage CSTR design are expected to outweigh the cost savings of a one-stage CSTR.

The disclosed process can be used for all aromatic amines which are diazotizable by reaction with nitrosyl fluoride under HF acid conditions. Such diazotizable aromatic amines include diazotizable carbo-cyclic aromatic primary amines (e.g. aminobenzenes) and heterocyclic aromatic primary amines (e.g. amino pyridines), including heterocyclic aromatic primary amines containing structures wherein benzene is condensed with a heterocyclic ring. Included by such amines are carbocyclic and heterocyclic mono-amines and carbocyclic and heterocyclic polyamines (e.g. diamines). Such amines include, for example, amines derived from such carbocyclic aromatic compounds as benzene, biphenyl, diphenylmethane, diphenyl ether, condensed benzenoids such as napthalene and anthracene and from such heterocyclic aromatic compounds as pyridine, quinoline and isoquinoline. The aromatic ring or rings of the aromatic amines may be unsubstituted or substituted with one or more substituents selected from the group consisting of alkyl (e.g. linear or branched alkyl having 1 to 12, preferably 1 to 4 carbon atoms), alkoxy (e.g. linear or branched alkoxy having 1 to 12, preferably 1-4 carbon atoms), halo (e.g. chloro, fluoro and bromo), nitro, cyano, acyl (e.g. linear or branched acyl having 1-4 carbon atoms such as acetyl), acylamino (e.g. acetylamino), carboxy and hydroxy.

Suitable carbocyclic aromatic primary amines include, for example, Niline; methoxyaniline (e.g. para-anisidine); chloroaniline and bromoaniline in which the chloro or bromo group is in the ortho, meta or para position relative to the amine group; toluidines such as ortho-, meta- and para-aminotoluene, and ring-halogenated (e.g. ring-chlorinated or ring-brominated) derivatives of such toluidines, e.g. 2-chloro-6-aminotoluene (also called 6-chloro-orthotoluidine); ortho-, meta- and para-phenylene diamine; methylene dianilines such as 3,3'-, 4,4'- and 3,4'-methylene dianiline; biphenyl amines, e.g. 2-aminobiphenyl, 4-amino-biphenyl, 3,3'-diamino-biphenyl, 4,4'-diamino-biphenyl and 3,4'-diaminobiphenyl; and ring-halogenated biphenyl amines, e.g. 3,3'-dichloro-4,4'-diamino-biphenyl (i.e., 3,3'-dichlorobenzidine, which rapidly undergoes diazotization). Suitable heterocyclic aromatic primary amines include, for example, 2-, 3- and 4-aminopyridine; diaminopyridines such as 2,6-diaminopyridine; haloaminopyridine such as 2-amino-4-, 5- and 6-chloropyridine and 3-amino-5 and 6-chloropyridine; nitroaminopyridines such as 2-amino-5-nitropyridine; and alkylaminopyridines such as 2-amino-4-, 5- and 6-methylpyridine and 2-amino-4, 6-dimethylpyridine.

In one preferred embodiment of this invention, the aromatic amine is aniline and the resulting diazotized amine is benzene diazonium fluoride, which can be decomposed to fluorobenzene (also called phenyl fluoride), which is useful as an intermediate for preparing insecticides, larvacides and tranquilizers. In another preferred embodiment, the armomatic amine is 6-chloro-ortho-toluidine and the resulting diazotized amine is 6-chloro-ortho-toluene diazonium fluoride, which can be decomposed to 2-chloro-6-fluorotoluene, which is useful as an intermediate for preparing herbicides and pharmaceuticals. In still another preferred embodiment, the aromatic amine is 4-fluoroaniline and the resulting 4-fluorobenzene diazonium fluoride can be decomposed to 1,4-difluorobenzene, which is useful as an intermediate for preparing herbicides.

Preferably, the amine is dissolved in a sufficient amount of HF such that all the amine will remain dissolved at 0° C. Such amount of HF is as follows for the indicated amines:

| Amine | Moles HF/Mole of Amine |
| --- | --- |
| Aniline | 6:1 |
| 2-chloro-o-toluidine | 6:1 |
| 4-fluoroaniline | 6:1 |
| Methylene dianiline | 9:1 |

The corresponding amounts for other amines can be readily determined by those skilled in the art.

The liquid amine-HF solution is formed using techniques in keeping with known methods for handling HF. Preferably, the solution is formed in a vessel having internal surfaces which are resistant to degradation by HF. Such surfaces may be formed, for example, of stainless steel and preferably polytetrafluoroethylene. The aromatic amine is added with stirring to sufficient liquid HF to prepare an amine-HF solution wherein the resulting dissolved amine will remain dissolved at between −10° and 0° C.

The diazotization solution which is introduced into each reactor in accordance with the process of the invention can be provided in the form of a solution in a suitable solvent. Preferably, the solution can be nitrosyl fluoride which is provided as a solution in HF. For the purposes of this description, the terms nitrosyl fluoride and diazotization solution are used interchangeably. To form the solution, a diazotization agent which contains or forms NO+ (the nitrosonium ion) is added with stirring to sufficient liquid HF to prepare a solution of nitrosyl fluoride in HF having a concentration such that all of the dissolved agent will remain dissolved at between about −10° and 0° C. Suitable diazotization agents include, for example, alkali metal nitrites (e.g. sodium nitrite and potassium nitrite), nitrous halides, nitrous oxide, nitrous acid and nitrous anhydride. Sodium nitrite is preferred. An amount of HF corresponding to a ratio of at least 12 moles of HF per mole of sodium nitrite has been found sufficient. Sufficient amounts of HF for other diazotization agents can be readily determined by those skilled in the art. This solution is premixed and preferably cooled before it is supplied to each CSTR.

It is known to those skilled in the art that hydrogen fluoride can act both as a reactant (e.g. a source of fluorine for the aromatic diazonium fluoride being prepared) and as the medium for the diazotization reaction. In the present case, in order to serve as the reaction medium, there is employed an amount of HF in excess of the amount of HF required for use as such reactant. The amount of HF employed in each solution preferably is such that the total amount of HF in the amine-HF solution and nitrosyl fluoride solution introduced into the reactor results in introduction of from about $(3+m)$ to about 30 moles and preferably from about $15+m$ to about 20 moles of HF per mole of introduced amine where m is the number of diazotizable —NH$_2$ groups per molecule of the amine. In general, amounts of HF less than $(3+m)$ moles per mole of amine result in unacceptably low autothermal decomposition temperatures, thereby risking uncontrollable reaction at otherwise desirable reaction temperatures and rates and/or requiring economically unacceptably low autothermal decomposition temperatures, thereby risking uncontrollable reaction at otherwise desirable reaction temperatures and rates and/or requiring economically unacceptable reductions in reaction temperature and rate to safeguard against such risk. Amounts of more than 30 moles of HF per mole of amine generally result in unacceptably slow preparation of aromatic diazonium fluoride and/or unacceptably high cost of HF recovery. The hydrogen fluoride may be added as aqueous hydrofluoric acid containing, for example, from about 3 to about 30 or more percent by weight of water, but preferably containing at least 70 percent by weight of HF (dry basis). However, better yields and greater freedom from tar, phenols and other by-products in subsequent decomposition of the diazonium fluoride to the aromatic fluoride can be obtained by employing at least substantially anhydrous hydrogen fluoride, i.e. not containing more than about 5% by weight water and preferably not more than 0.1% water.

The aromatic amine-HF solution is continuously introduced into a first continuous-stirred tank reactor connected in series via an overflow pipe to a second reactor. This reactor, in turn, can be connected by an overflow pipe to a third reactor, the third to a fourth, and so on. It is recommended that at least two, but preferably 3, reactors be sequentially connected. The amine solution is preferably introduced into the first reactor at a temperature not substantially greater than 0° C.

The diazotization solution preferably is introduced in a parallel fashion into each of the sequentially connected reactors. It also preferably is introduced at a temperature not substantially greater than 0° C.

Figure 2:
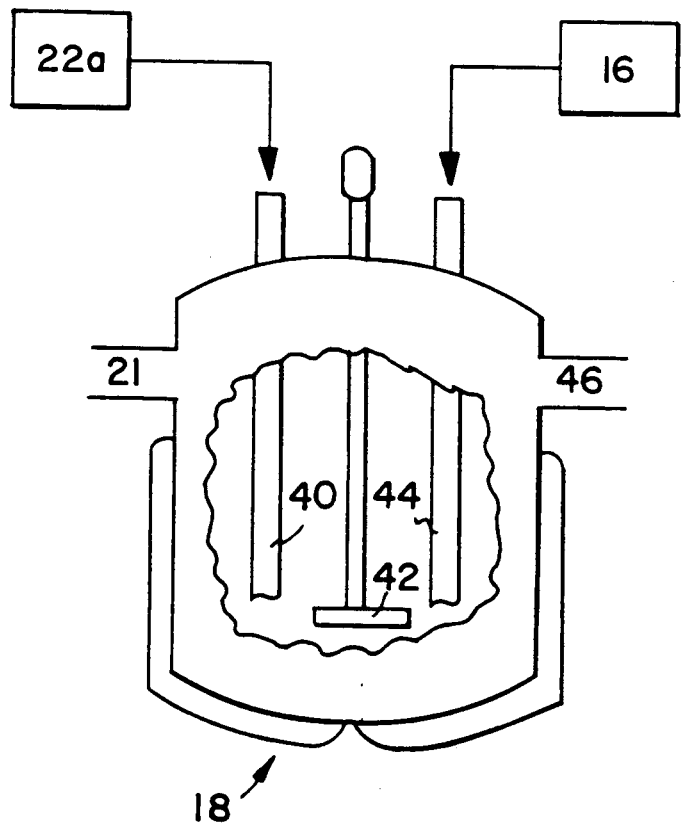
FIG. 2 is a schematic illustration of the process showing the feeding of the diazotization solution directly into the radial discharge zone of a radial turbine.
Figure 3:
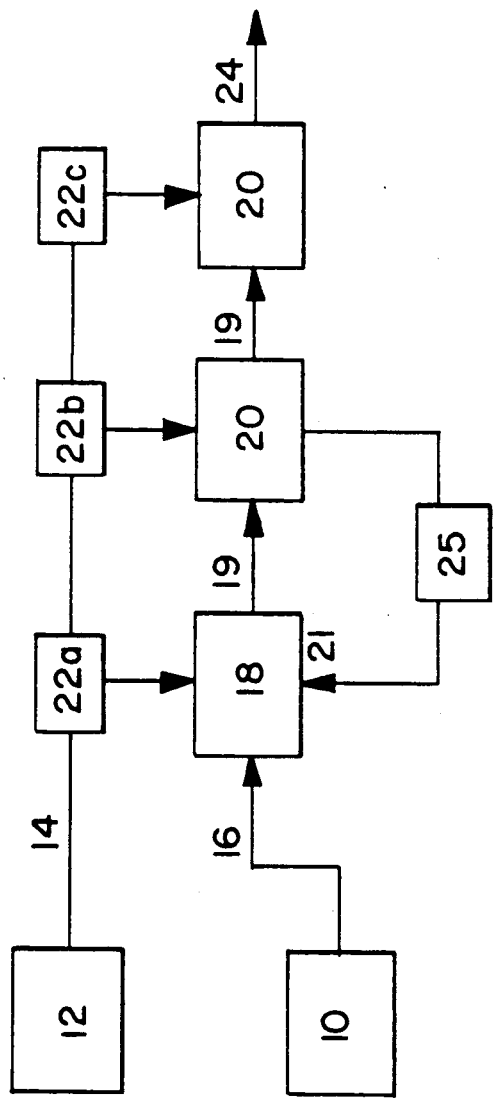
FIG. 3 includes a schematic illustration of a feedback loop from a subsequent reactor to a prior reactor.

In a specific example of one embodiment of the invention, as shown in FIG. 2, each reactor is a continuous-stirred tank reactor (CSTR) having a submerged inlet pipe 40 for continuous injection of a diazotization solution to a vessel agitator such as a radial turbine 42. This vessel agitator provides rapid mixing of the amine-HF and diazotization solutions entering through conduits 44 and 40, respectively. An overflow outlet 46 for passing diazotized amine to the next reactor or to a decomposition chamber is provided. Optionally, if the reactor is one of the initial reactors in the reactor sequence, it can have an additional inlet for a feedback solution 21 (also shown in FIG. 3) from subsequent reactors. As shown in FIG. 3, ordinarily, this feedback solution 21 will enhance the temperature control of the prior reactor because it will have been passed through a cooling means 25 prior to being fed back into the upstream reactor. Such cooling means are known to those of skill in the art. Typically, the agitation is selected to provide a maximum rate of dispersion of seed from the inlet pipes. Suitable agitators include radial types, multiple paddles or turbines. Alternative designs for mixing can also be used. Such designs include, for example, a pump around loop.

While passing a flow of amine-HF solution through the series of reactors, a flow of diazotization solution is continuously fed directly to the radial discharge zone of the radial turbine of each reactor at a temperature of not substantially more than 0° C. Injection into this radial discharge zone enhances the rapid and intimate mixing of the amine-HF solution with the diazotization solution. A reaction mixture will be formed in each reactor which can be different depending upon the composition of the overflow input. In each reactor, an amount of amine which is approximately stoichiometrically equivalent to the amount of diazotization solution injected through the diazotization solution inlet thereof is diazotizingly reacted to (a) prepare a quantity of aromatic diazonium fluoride and (b) generate a corresponding amount of heat. The ratio of total flow rate of diazotization solution to flow rate of amine solution corresponds to from about 0.9 to about 1.0 mole of diazotization solution per molar equivalent of amine. Preferably, the total amount of HF in the introduced amine-HF solution and injected diazotization solution is such that there are introduced from about $(3+m)$ to about 30 moles of HF per mole of amine where m is the number of diazotizable —NH$_2$ groups per molecule of said amine.

Optimally, heat is removed from each reactor in a sufficient amount and at a sufficient rate of heat transfer such that the maximum temperature of the diazonium-fluoride-containing reaction mixture therein is less than the lower of (i) the autothermal decomposition temperature of said mixture, and (ii) the temperature at which said diazonium fluoride decomposes to such an extent and at such a rate that said aromatic diazonium fluoride is present in the reaction mixture exiting the reactor in an amount 5% less than the amount present when maximum temperature in each reactor is at 15° C. Heat is removed to avoid the initiation of both an autothermal decomposition and measurable decomposition. Generally, the upper temperature for incipient decomposition of the diazonium is avoided by choosing an operating temperature that produces at least about 98% conversion of the diazotizer introduced to that stage, and at a diazonium yield greater than about 95% and having no measurable decomposition products. For example, for aniline and benzenediazonium, an operating temperature that produces more than 95% of the expected diazonium when each reactor is at 15° C. is desirably selected.

Using the disclosed process, diazonium fluoride can be prepared in an amount corresponding to at least 95% yield based on a molar ratio with the amount of diazotization solution employed. The resulting mixture exiting the last reactor is substantially free of diazotization solution and the diazonium fluoride in the resulting mixture subsequently can be decomposed with substantial freedom from formation of tar and other by-products to produce the desired aromatic fluoride.

The ratio of the flow rate of the diazotization solution to the flow rate of the amine-HF solution is maintained at an amount corresponding to slightly less than 1.0 mole of the diazotization solution per molar equivalent of the amine and preferably at about 0.98 mole of diazotization solution per molar equivalent of the amine. The total amount of HF in the two solutions is controlled such that there are introduced from about 3+m to about 30 moles of HF per mole of amine where m is the number of diazotizable —NH$_2$ groups per molecule of the amine.

Although the individual flow rates of nitrosyl fluoride solution introduced through each inlet into each reactor may be unequal, preferably such rates are equal to one another. As a general preference, the n reactors are of the same type and approximately 1/n of the total flow of nitrosyl fluoride solution is introduced through an inlet into each of the n reactor, n being defined above. Thus, the premixed diazotization solution can be fed to a solution splitter, 22 in FIG. 1, and split into separate streams.

In general, from about 98% to about 100% of the introduced nitrosyl fluoride is converted to the corresponding diazonium fluoride.

Removal of heat can be by any effective means. Examples include a cooling bath, of a type known to those of skill in the art, into which the reactor is immersed. Preferably, heat removal is effected by means of flowing a coolant (e.g. 50% glycol and 50% water supplied at minus 5° C. or less) through separate external cooling jackets which surround each reactor and function as heat exchangers.

Means of temperature control other than heat removal from the reaction zones also can be employed to control the temperature of the reaction mixture. For example, a portion of the product emerging from any reactor in the sequence prior to the last reactor can be recycled to an inlet into itself or one or more of the upstream reactors, after passing it through a heat exchanger to reduce its temperature. It has been found that product emerging from the last stage should not be recycled, especially where the last 5 to 15% of the diazotizer is injected, because of a rapid decline of reaction rate. The recycled mixture will absorb heat from the reaction mixture in the reactor into which it is introduced, thereby assisting in the control of temperature in that reactor.

It is critical that the maximum temperature of the reaction mixture containing diazonium fluoride be maintained at less than the autothermal decomposition temperature of the mixture. For a given system, such temperature decreases with increasing concentration of the diazonium fluoride being prepared. In general, the concentration of diazonium fluoride safely may be up to about 3 gram-moles per liter (g-moles/l), e.g. from about 0.1 to 3 g-moles/l, preferably from about 1.5 to 2.5 g-moles/l and more preferably from about 2.0 to 2.5 g-moles/l.

Where aniline is the amine being diazotized and the resulting benzene diazonium fluoride is present in a concentration of up to about 2.5 g-moles/l in the reaction mixture exiting the last reactor, the maximum temperature of the reaction mixture in the reactors corresponding to approximately 40% of the upstream length of the sequential series may be up to about 25° C., while the maximum temperature of the reaction mixture in the downstream remainder of the sequence may be up to about 15° C. The indicated temperatures may be held at or below such maximums by balancing the heat load (which depends on rate of reaction and flow rate) and heat removal capacity of the temperature control system. Suitable temperatures for other diazoniums can be determined by those of skill in the art.

According to Behringer, et al., U.S. Pat. No. 4,268,437, incorporated herein by reference, if an amine rapidly undergoes diazotization, it is good practice to introduce the aqueous sodium nitrite solution exclusively through one inlet in the continuous diazotization process disclosed therein. By contrast, in the disclosed process, a solution of nitrosyl fluoride in HF is advantageously introduced through a plurality of inlets for all amines, including amines which rapidly undergo diazotization (e.g. 3,3'-dichlorobenzidine, aniline, 2-chloro-o-toluidine, 4-fluoroaniline and methylene dianiline).

The heat capacity of HF is approximately half the heat capacity of water. Therefore, a given heat load (e.g. amount of generated heat of diazotization) has the potential to increase the temperature of a given mass of HF by an amount which is approximately double the potential temperature increase for a like mass of water. This phenomenon is sometimes referred to by those of skill in the art as the double delta-T effect.

It will be appreciated by those skilled in the art that this double delta-T effect results in a considerably greater temperature-control burden on the present process relative to diazotization processes carried out in predominantly aqueous media (a number of which are referenced above), especially where as preferred in the present process at least substantially anhydrous hydrogen fluoride is employed. Advantageously, the disclosed process effectively bears such burden without detracting from the effective utility thereof. In general, the flow rate of the amine-HF solution is such that the average residence time thereof in each reactor is from about 0.5 minutes to about 15 minutes.

Practice of this invention is further illustrated by the following non-limiting example. All parts, percents and other amounts throughout this disclosure are by weight unless otherwise indicated. However, the specific conditions will be determined by the operating temperature, the concentration at the particular stage, and the specific diazonium species being synthesized. Such conditions can be determined without undue experimentation by those of skill in the art.

EXAMPLE

A 10-liter solution of NOF/HF was premade at a concentration of 4.85 gmole/liter. Also premade was a 10-liter solution of aniline/HF at 5.63 gmole/liter. The two feedstocks were held in separate 15-liter, agitated and jacketed vessels in which their temperatures were maintained at 15° C. Each vessel was placed on a scale for timed weight additions.

The reaction system consisted of three, one liter, agitated Parr reactors. Each reactor was immersed up to the top flange in separate glycol baths. The glycol level was such that all of the resulting diazonium solution was in contact with cooling transfer area. The individual baths were maintained at $-7°$ C. to $5°$ C. by using a combination of dry ice ($CO_2$) and an agitator in the bath.

Each Parr reactor was sequentially interconnected with another, such that reactor #1 had an aniline/HF injection, an NOF/HF injection and an overflow. Reactor #2 and #3 each had an inlet from the previous reactor, an NOF/HF injection and an overflow.

Into each reactor was precharged one liter of aniline/HF. The aniline/HF in each vessel was then allowed to equilibrate to the temperature of the immersion bath prior to initiating the NOF/HF flow.

Three Teflon rotameters were used to split the NOF/HF streams, such that 60% of the total flow was injected into reactor #1, 30% into reactor #2, and 10% into reactor #3. The total NOF/HF flow was maintained at an average 52.9 g/min, or 0.171 gmole/min. A gear pump was utilized to feed the total NOF/HF flow to the rotameters.

At time zero the NOF/HF was injected simultaneously in the appropriate relative proportions into reactors #1, #2, and #3. After approximately 10 minutes each reactor had established the desired 15° C. operating temperature. Continual additions of dry ice and adjustments to the agitation rate in the glycol baths were required to properly maintain a temperature of 15° C. in each reactor. After temperature equilibrium was reached, the aniline/HF flow, also fed by a gear pump, was initiated at an average flow rate of 37.2 g/min., or 0.175 gmole/min. Based on the gmole/min flow of each reactant, the expected conversion of aniline to diazonium was 97.7%.

The flows and temperatures were maintained for three hours after the aniline/HF flow was initiated. At that time all three reactors had attained steady state concentrations. Samples were pulled from the overflow of all three reactors, and analyzed for aniline, benzene diazonium, and NOF.

Based on these samples the conversion of aniline to diazonium based on NOF injection was 100% for reactor #1. The conversion of aniline to diazonium, based on NOF injected, was 99% for reactor #2. The conversion of aniline to diazonium, based on the NOF injected and the effluent from reactor #2, was 95% for reactor #3. The total conversion of aniline to diazonium for the entire CSTR system, based on NOF injected, was 99.5%. The total conversion of aniline to diazonium based on the aniline injected was 97.2%.

What is claimed is:

1. A process for the continuous production of an aromatic diazonium fluoride compound from a corresponding aromatic amine which comprises:
   (a) pre-mixing a diazotizing agent and hydrogen fluoride such that a diazotization solution is made;
   (b) removing heat from said diazotization solution so as to form a cooled diazotization solution;
   (c) continuously introducing through a parallel series of inputs a flow of said cooled diazotization solution into each of a series of sequentially linked continuous-stirred tank reactor;
   (d) continuously introducing into the first of said reactors in said series of reactors a flow of an amine solution comprising an aromatic amine-hydrogen fluoride solution, said aromatic amine-hydrogen fluoride solution overflowing from said first reactor into each subsequent reactor in a serial flow;
   (e) mixing said aromatic amine-hydrogen fluoride solution with said diazotization solution in each reactor in said series of reactors, to form a reaction mixture, thereby reacting said amine and said diazotizing agent to form an aromatic diazonium fluoride; and
   (f) removing heat from each of said reactors in said series of reactors, such that each reactor is at a temperature less than a temperature at which autothermal decomposition of said diazonium fluoride takes place.

2. A process as claimed in claim 1, wherein said diazotization solution comprises nitrosyl fluoride.

3. A process is claimed in claim 2, wherein the ratio of the flow rate of said aromatic amine-hydrogen fluoride solution into the first reactor to the sum of the flow rate of said diazotization solution into each of the reactors is such that at least 95% of the nitrosyl fluoride is reacted to form diazonium fluoride.

4. The process of claim 2, wherein the nitrosyl fluoride is formed by dissolving in liquid hydrogen fluoride a diazotization agent selected from the group consisting of alkali metal nitrite, nitrous acid, nitrous anhydride, nitrous halide, and nitrous oxide.

5. The process of claim 2, wherein said aromatic amine is selected from the group consisting of carbocyclic aromatic primary amines and heterocyclic aromatic primary amines.

6. The process of claim 5, wherein said carbocyclic amines are derivatives of carbocyclic compounds selected from the group consisting of benzene, biphenyl, diphenylmethane, diphenyl ether, napthalene and anthracene, and said heterocyclic amines are derivatives of heterocyclic compounds selected from the group consisting of pyridine, quinoline and isoquinoline.

7. The process of claim 5, wherein said carbocyclic amines are selected from the group consisting of aniline, methoxyaniline, chloroaniline, bromoaniline, toluidine, ring-halogenated toluidine, phenyl diamine, methylene dianiline and biphenyl amine, and said heterocyclic amines are selected from the group consisting of aminopyridine diaminopyridine, haloaminopyridine, nitroaminopyridine and $C_1$ to $C_8$, alkylaminopyridine.

8. The process of claim 5, wherein said aromatic amine is selected from the group consisting of aniline, 2-chloro-toluidine, 4-fluoroaniline and methylene dianiline.

9. The process of claim 8, wherein said amine is aniline and said diazonium fluoride is benzene diazonium fluoride.

10. The process of claim 2, further comprising after the aromatic diazonium fluoride-containing mixture exits the last reactor in said series, decomposing the aromatic diazonium fluoride, thereby forming the corresponding aromatic fluoride with substantial freedom from formation of tar and other byproducts.

11. The process of claim 2, wherein said sequentially-linked reactors comprise n reactors, wherein n is an integer having a value of at least 2.

12. The process of claim 11 wherein n is at least 3.

13. The process of claim 2, wherein said amine is aniline, said aromatic diazonium fluoride is benzene diazonium fluoride which is present at a concentration of up to about 2.5 gram-moles per liter in the reaction mixture exiting the last reactor in said series of reactors, the maximum temperature of the reaction mixture in the first reactor in said series is about 25° C., and the maximum temperature of the reaction mixture in the other reactors in said series is about 15° C.

14. The process of claim 12, wherein the aniline-HF solution comprises at least 6 moles of HF per mole of aniline, the solution of nitrosyl fluoride is prepared from sodium nitrite and HF in an amount corresponding to at least 12 moles of HF per mole of sodium nitrite, said series of reactors comprises at least 2 reactors, and the average residence time of the anine-HF solution in each reactor is from 0.5 to 15 minutes.

15. The process of claim 2, wherein a portion of the product exiting one or more of the intermediate reactors is passed through a heat exchanger to reduce its temperature and then recycled to the reactor from which it was removed or a preceding reactor in said series of reactors.

16. The process of claim 2, wherein said diazotization solution is fed directly to a vessel agitator in each of said reactors in said series.

17. The process of claim 16 wherein said vessel agitator comprises a radial turbine having a radial discharge zone.

18. The process of claim 17, wherein said solution is fed directly to the radial discharge zone of said radial turbine in each of said reactors in said series.

* * * * *